US 10,874,778 B2

(12) United States Patent
Camisani et al.

(10) Patent No.: US 10,874,778 B2
(45) Date of Patent: Dec. 29, 2020

(54) SEQUENTIAL PROCESSING OF BIOLOGICAL FLUIDS (71) Applicant: BioSafe S.A., Eysins (CH)

(72) Inventors: Julien Camisani, Preverenges (CH); Oliver Link, Geneva (CH)

(73) Assignee: BioSafe S.A., Eysins (CH)

( * ) Notice: Subject to any disclaimer, the term of this patent is extended or adjusted under 35 U.S.C. 154(b) by 0 days.

(21) Appl. No.: 16/559,443

(22) Filed: Sep. 3, 2019

(65) Prior Publication Data

US 2019/0388596 A1 Dec. 26, 2019

Related U.S. Application Data (63) Continuation of application No. 15/537,053, filed as application No. PCT/IB2015/057527 on Oct. 1, 2015, now abandoned.

(30) Foreign Application Priority Data

Dec. 19, 2014 (CH) ........................ 1985/14

(51) Int. Cl.
A61M 1/02 (2006.01)
A61M 1/36 (2006.01)
(Continued)

(52) U.S. Cl.
CPC ........... *A61M 1/029* (2013.01); *A01N 1/0221* (2013.01); *A61K 35/14* (2013.01); *A61M 1/0209* (2013.01);
(Continued)

(58) Field of Classification Search
CPC ... A01N 1/0221; A61K 35/14; A61M 1/0209; A61M 1/0272; A61M 1/0281;
(Continued)

(56) References Cited

U.S. PATENT DOCUMENTS 3,823,724 A 7/1974 Davis
6,733,433 B1 5/2004 Fell
(Continued)

FOREIGN PATENT DOCUMENTS

CN 2601095 Y 1/2004
CN 101146559 A 3/2008
(Continued)

OTHER PUBLICATIONS

First Office Action for Chinese Patent Application No. 201580069285, filed Oct. 1, 2015, dated Mar. 21, 2019.
(Continued)

*Primary Examiner* — Timothy C Cleveland
(74) *Attorney, Agent, or Firm* — Eversheds Sufherland (US) LLP (57) ABSTRACT A process for the sequential processing of opaque and transparent biological fluids such as whole blood, apheresis blood, bone marrow blood, umbilical cord blood, buffy coat or cultured cells by processing steps in a hollow cylindrical centrifugal processing chamber (300) which is part of a disposable set. At least three different procedures selected from washing, incubation, transduction, separation, density gradient separation, dilution and volume adjustment are each carried out once or repeated a number of times according to a given processing profile in the processing chamber. Each procedure involves an input into the processing chamber, an operation in the processing chamber and an output from the processing chamber by displacement of a piston (310). The at least three different procedures are sequentially chained one after the other to constitute an overall sequential operation in the processing chamber and its disposable set. A first application is incubation for binding magnetic beads with human blood cells or stem cells. A second application is transduction by which foreign genetic material is inserted (Continued)

into human blood cells or stem cells by a virus. A third application is reconditioning biological fluids to achieve reproducible concentration and volumes of blood cells or stem cells.

14 Claims, 5 Drawing Sheets

(51) Int. Cl.
*A01N 1/02* (2006.01)
*A61K 35/14* (2015.01)
*B04B 5/04* (2006.01)

(52) U.S. Cl.
CPC ........ *A61M 1/0272* (2013.01); *A61M 1/0281* (2013.01); *A61M 1/3618* (2014.02); *A61M 1/3692* (2014.02); *A61M 1/3693* (2013.01); *A61M 1/3698* (2014.02); *A61M 2205/3313* (2013.01); *B04B 2005/0485* (2013.01)

(58) Field of Classification Search
CPC .. A61M 1/029; A61M 1/3618; A61M 1/3692; A61M 1/3693; A61M 1/3698; A61M 2205/3313; B04B 5/0428; B04B 5/0442; B04B 2005/0485
See application file for complete search history.

(56) References Cited

U.S. PATENT DOCUMENTS

| | | |
|---|---|---|
| 2007/0166291 A1 | 7/2007 | Benati |
| 2008/0171951 A1 | 7/2008 | Fell |
| 2014/0315311 A1 | 10/2014 | Miltenyi et al. |

FOREIGN PATENT DOCUMENTS

| | | |
|---|---|---|
| EP | 0144026 A2 | 6/1985 |
| EP | 0912250 | 5/1999 |
| EP | 01144026 B1 | 7/2004 |
| WO | 2009072003 | 5/1997 |
| WO | 2016073602 A2 | 5/2016 |

OTHER PUBLICATIONS

European Search Report from EP Application No. 191693445.6, dated Jul. 18, 2019.

SEQUENTIAL PROCESSING OF BIOLOGICAL FLUIDS

FIELD OF THE INVENTION

The invention relates to a system for the processing of biological fluids such as whole blood, apheresis blood, bone marrow blood, umbilical cord blood, buffy coat or cultured cells by process steps which include washing, incubation, transduction, separation, density gradient separation, dilution and volume adjustment.

BACKGROUND OF THE INVENTION

EP-B-0 912 250 (C.FELL), the contents whereof are herein incorporated by way of reference, describes a system for the processing and separation of biological fluids into components, comprising a set of containers for receiving the biological fluid to be separated and the separated components, and optionally one or more additional containers for additive solutions. A hollow centrifuge processing chamber is rotatable about an axis of rotation by engagement of the processing chamber with a rotary drive unit. The processing chamber has an axial inlet/outlet for biological fluid to be processed and for processed components of the biological fluid. This inlet/outlet leads into a separation space of variable volume wherein the entire centrifugal processing of biological fluid takes place. The processing chamber comprises a generally cylindrical wall extending from an end wall of the processing chamber, this generally cylindrical wall defining therein the hollow processing chamber which occupies a hollow open cylindrical space coaxial with the axis of rotation, the axial inlet/outlet being provided in said end wall coaxial with the generally cylindrical wall to open into the hollow processing chamber. The processing chamber contains within the generally cylindrical wall an axially movable member such as a piston. The separation space of variable volume is defined in an upper part of the processing chamber by the generally cylindrical wall and by the axially movable member contained in the generally cylindrical wall of the processing chamber, wherein axial movement of the movable member varies the volume of the separation space, the movable member being axially movable within the processing chamber to intake a selected quantity of biological fluid to be processed into the separation space via the inlet before or during centrifugal processing and to express processed biological fluid components from the separation space via the outlet during or after centrifugal processing. Means are provided for monitoring the position of the movable member to thereby control the amount of intaken biological fluid and the expression of separated components. The system further comprises a distribution valve arrangement for establishing selective communication between the processing chamber and selected containers or for placing the processing chamber and containers out of communication.

According to EP-B-1 144 026, such a system is arranged to operate in a separation and in a non-separation transfer mode, which provides greater possibilities for use of the system including new applications which were previously not contemplated, such as separation of hematopoietic stem cells and in general laboratory processing.

The system according to EP-B-0 912 250 and EP-B-1 144 026 is designed to operate for the separation of biological fluids, and has proven to be very polyvalent for many separation applications, especially for on-line separation of components from a donor or a patient, using a processing or mixing chamber which is part of a disposable set constituting an enclosed sterile environment. This system has been commercialized by Biosafe SA under the Trademark Sepax.

The Sepax system was used in the past for processing mainly blood and blood derivatives products containing adult stem cells such hematopoietic, mesenchymal or adipose-derived stem cells suspended in a buffy coat coming from blood sources such as bone marrow, cord blood or peripheral blood after patient mobilization.

The most typical application so far has been volume reduction processing of blood or blood derivatives. By doing so, the plasma and most red blood cells are depleted and the buffy coat layer, comprising essentially white blood cells and stem cells suspended in remaining plasma and red blood cells, is collected in a selectable volume. Based on the final volume chosen, more plasma and red blood cells can be added according to user's needs.

A second application where the Sepax technology is often used is the washing application. Stem cells concentrated products are usually cryo-preserved if there are not used within typically 48 hours. Once a cellular product containing stem cells is needed for transplantation, a thawing procedure is done and then a washing procedure is recommended to be performed for eliminating side-effects during transplantation generated by the residual toxic dimethylsulfoxide (DMSO).

A third application consists of mixing a density gradient medium with the desired product wanted to be volume reduced. During sedimentation, the gradient density medium will create a layer after the plasma and monocyte and lymphocyte cell population, but before granulocytes and red blood cells during the centrifugation process. Sepax technology is able to extract the white blood cells and stem cells suspended in a medium free of red blood cells. This is particularly suitable for transplantations when there is a minor or major incompatibility between donor and receiver.

Most applications performed with Sepax technology so far were focussing on processing blood and blood derivatives containing stem cells and having a limited volume below usually much lower than 880 ml. Also, the known Sepax applications were essentially limited to performing most often one single processing function with the product, such as volume concentration or washing applications. Another limitation of Sepax was that the products to be processed all contained red blood cells in the product, and the apparatus used an optical sensor as an essential element essential for determining the transition between red blood cells and the in-piston gap.

Other systems are known for processing biological fluids, for example that of WO 2009/072003 comprising a sample processing unit including a centrifugal bowl and a coupled sample separation unit. Such systems can carry out sequential processing procedures but their configuration and operation are so different from the Sepax system that they offer no useful guidance for improving the Sepax system with its inherent limitations.

SUMMARY OF THE INVENTION

The invention relates to a process for the sequential processing of opaque and transparent biological fluids such as whole blood, apheresis blood, bone marrow blood, umbilical cord blood, buffy coat or cultured cells by process steps including washing, incubation, transduction, separation, density gradient separation, dilution and volume adjustment in a hollow cylindrical centrifugal processing or mixing chamber for processing the biological fluids and/or mixing of the biological fluids with reagents and/or diluents, wherein the centrifugal processing chamber contains within its generally cylindrical wall an axially movable member such as a piston which is axially movable to vary the volume of a separation space within the processing chamber to intake or to output biological fluids into or from the separation space, wherein the processing chamber is part of a disposable set containing the biological fluids and reagents and/or diluents, the disposable set constituting an enclosed sterile environment.

According to the invention, using a single processing chamber as part of a disposable set, at least three different procedures selected from washing, incubation, transduction, separation, density gradient separation, dilution and volume adjustment are carried out, each procedure being carried out once or repeated a number of times according to a given processing profile in the processing chamber. Each said procedure involves an intake into the processing chamber produced by axially moving the movable member, an operation in the processing chamber, and an output from the processing chamber produced by axially moving the movable member. The at least three different procedures are sequentially chained one after the other in the processing chamber to constitute a chained sequence of the different procedures as an overall sequential operation in the processing chamber and its disposable set. All of the biological fluids, reagents and/or diluents necessary for carrying out all of said at least three different procedures are contained in the enclosed sterile environment of the single disposable set used for the overall sequential operation.

In one application, the following procedures are carried out sequentially: pre-washing; addition of reagents and incubation; post-washing. This application is for example for binding magnetic beads with human blood cells or stem cells.

In another application, the following procedures are carried out sequentially: washing; dilution; centrifugal separation; dilution; volume adjustment of the product. This application is for example for virus transduction with lymphocytes T-cells or other human cells.

In yet another application, the following procedures are carried out sequentially: preliminary thawing; washing; sampling and dilution; volume adjustment/extraction. This application is for example for recondition dosing of multiple doses of cellular products.

By way of explanation, the various procedures usually involve the following steps.

A washing procedure typically involves the following steps: filling the processing chamber with the cell-based product, filling the remaining capacity of the processing chamber with a washing solution, spinning at a given G force and during a given time t, extracting the washing solution in a waste bag and finally extracting the desired final volume containing cells in the output collection bag.

An incubation procedure typically involves the following steps: filling the processing chamber with the cell-based product, filling the processing chamber with incubation beads, performing the incubation by bi-directional mixes of the processing chamber at regular time intervals and finally extracting and collecting the incubated product in a collection bag.

A transduction procedure typically involves the following steps: filling the cell product in the processing chamber with cell-based product, filling the processing chamber with the biological virus, spinning at a given G force and during a given time t for performing the transduction, extracting the transduced product in the output collection bag.

A separation procedure typically involves the following steps: filling the processing chamber with the cell-based product, product separation into components by spinning at a given G force and during a given time t, extraction out of the chamber unwanted components in waste bags and component layer containing cells in the output collection bag.

A density gradient procedure typically involves the following steps: filling the spinning processing chamber with the gradient density medium, slowly filling the spinning processing chamber with the cell-based product, separation of the solution into components by spinning at a given G force and during a given time t, extraction out of the chamber unwanted components in waste bags and component layer containing cells and part of the gradient density medium in the output collection bag.

A concentration procedure typically involves the following steps: filling the processing chamber with the cell-based product, concentration of cells by centrifuging at a given G force and during a given time t, extraction out of the chamber unwanted components in waste bags and by collecting compacted cells in the output collection bag.

A dilution procedure typically involves the following steps: Characterization of the initial cell-based product if a desired final cell concentration needs to be achieved; filling the processing chamber with the cell-based product; continue filling the processing chamber with a pre-calculated volume of a saline solution, or for suspending cells in a medium and nourishing solution, based on the volume or cell concentration dilution ratio desired; bi-directional mixes of the processing chamber at regular time intervals for mixing the diluted or suspended cell solution during the filling and extraction of fluid from the processing chamber; extraction out of the chamber the diluted cell solution in the output collection bag. An alternative processing option is to fill the processing chamber with the calculated volume of saline or medium solution based on the dilution ration desired, and then extracting the saline or medium solution out of the chamber in the output collection bag containing the cellular product.

A volume adjustment procedure typically involves the following steps: filling the processing chamber with the cell-based product or the pre-diluted solution, selecting the output volume and the number of doses desired, extraction of the multiple doses out of the processing chamber by automatically switching to different bags or by making a pause after each dose and asking the user to select the destination bag where the next dose should be extracted.

The processing chamber usually includes a movable piston, and the position of the piston (or other movable member) is monitored by an infrared sensor.

The volume of liquids treated in the processing chamber for one overall sequential operation can be up to sixteen times the maximum treatment volume of the processing chamber. For instance the volume for one overall sequential operation can be four times, eight times or sixteen times the maximum treatment volume of the processing chamber which can be represented by the maximum volume of the aforesaid separation space in the processing chamber.

The processing chamber is advantageously associated with two external pinch valves controlling tubing of the disposable set for selecting two biological additives for switching bags of the disposable set without user intervention.

The system for performing the inventive process typically comprises a cabinet housing the hollow centrifugal or mixing processing chamber of the disposable set, for example according to the known Sepax technology.

One advantage of the inventive process chaining different procedures is that it can handle greater volumes than heretofore possible, for example up to 4 litres whereas the previously processed volume was up to 880 ml. It thus overcomes the volume limitation of Sepax technology as previously proposed.

Also, it has been made possible to extend processing to all types of white blood cells (platelets, monocytes, lymphocytes, granulocytes) whereas previous processing was confined essentially to stem cells and red blood cells. This has been made possible by using an infrared sensor with an algorithm designed for accurately measuring the piston position while processing transparent fluid, replacing the former optical sensor used for red blood cells.

The Sepax system is advantageously completed by two pinch valves for automatically selecting, by software, two biological additives such as virus, for priming the chamber and later switching with the medium solution for resuspension, for switching bags without user intervention.

A first application of the invention consists of incubation for binding magnetic beads with human blood cells or stem cells, like lymphocytes T cells, B cells or hematopoietic stem cells. A second application is transduction by which foreign genetic material is inserted into human blood cells or stem cells by a virus. A third application refers to reconditioning biological fluids to achieve reproducible concentration and volumes of blood cells or stem cells.

BRIEF DESCRIPTION OF DRAWINGS

The invention will be further described by way of example, with reference to the accompanying drawings wherein.

DETAILED DESCRIPTION

Application 1: Binding Magnetic Beads with Human Blood Cells or Stem Cells

The first application relates to the blending of magnetic beads of human blood cells or stem cells, like lymphocytes T cells, lymphocytes B cells or hematopoietic stem cells with magnetic beads.

This application illustrates the sequential carrying out of the following procedures: washing, dilution, incubation and washing.

The first stage is to precondition the cell-based product, usually coming from an apheresis procedure for collecting peripheral blood stem cells and rarely also coming from bone marrow harvesting, in order to get rid of unnecessary elements such as human platelets, aggregates, clots, cell debris but also to hydrate the cells by adding biological nutriments. Cryo-protectant solution like Dimethyl sulfoxide should also be removed via this stage if the product was previously cryopreserved.

Then, the second step relates to adding a dose of reagents, like magnetic beads, or coloration medium, or a dose of stain to the preconditioned biological products.

The third step relates to incubation of the solution. The purpose of this step is to bind magnetic beads to targeted cells, or to colorize activated cells to make them highly sensitive to photodynamic treatment, or to bind other solutions via varied mechanism with targeted cells. During this phase, incubation can be done at ambient temperature during a given time, usually starting from 10 minutes up to 2 hours with a typical time of 30 minutes, in a separation chamber while constantly mixing the solutions. It can also be done under a controlled temperature, time and constant mixing in a blood bag via a device, for example that described in WO 2014/181158 A1, and commercialised by Biosafe SA under the Trademark Smart-Max. Such devices serve for mixing biological specimens contained in flexible storage bags at controlled temperature, which flexible storage bags may serve, in addition to storage, for the collection, freezing storage or transfer of biological specimens.

Finally, the last step is another washing step for the removal of excess reagents, like unbound magnetic beads not attached to targeted cells to avoid incorrect selection or counting of targeted cells, or to stop the coloration process by medium exchange, or to remove other solutions via the supernatant followed by suspension of cells in fresh medium.

All those steps are done are done sequentially under an automated system and in a sterile environment for instance using the aforementioned Sepax technology.

Figure 1A:
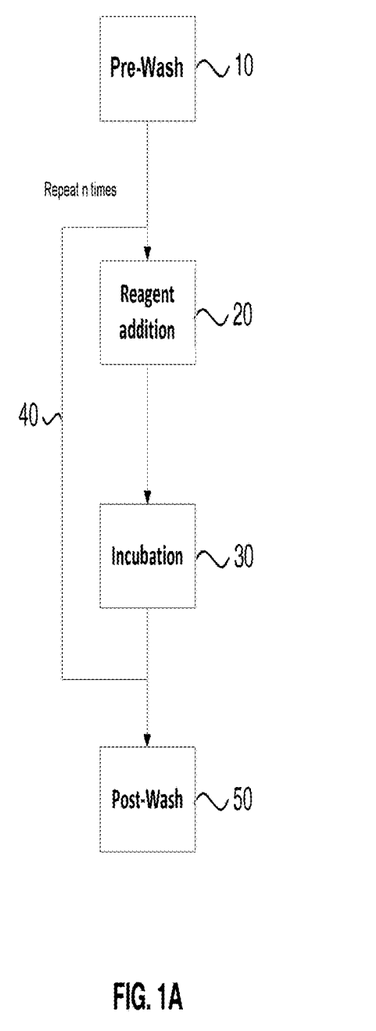
FIG. 1A is a flow diagram of a first application of the invention.
Figure 1B:
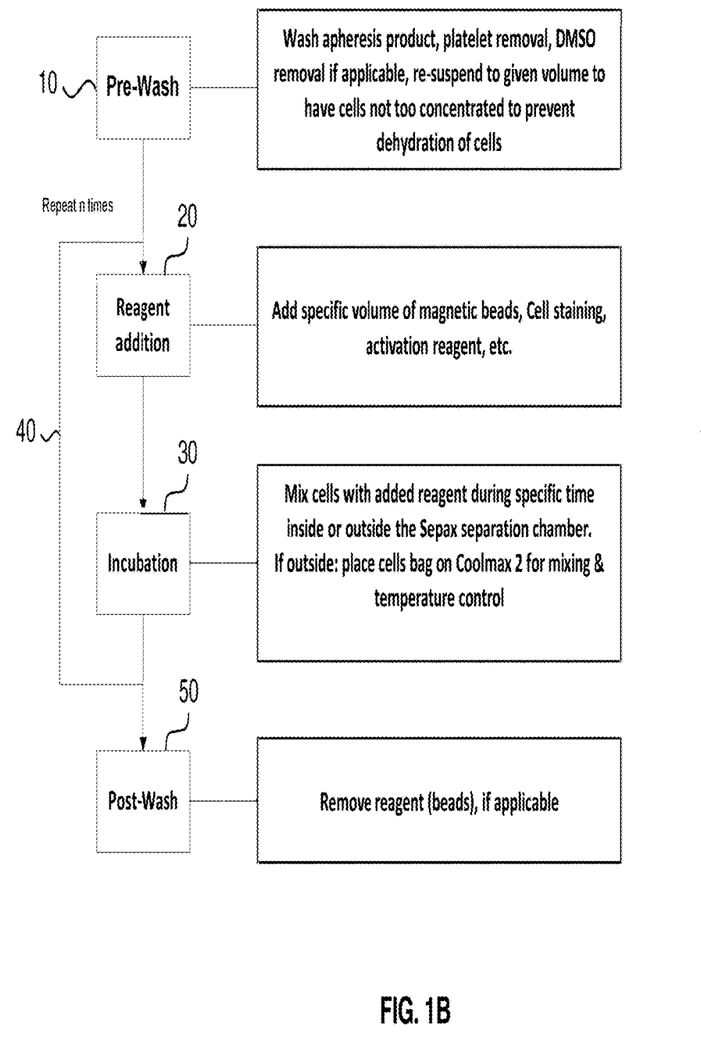
FIG. 1B is a completed diagram of the first application.

This first application is illustrated in FIG. 1A and FIG. 1B. As shown in FIG. 1A, this application of the process includes a pre-wash step 10, followed by reagent addition 20 and incubation 30. The reagent addition 20 and incubation 30 are repeated n times via loop 40. Then the final incubated product is subjected to a post-wash step 50.

As shown in FIG. 1B:

The pre-wash step 10 involves washing a cell-based product typically from an apheresis procedure, platelet removal, and DMSO removal if applicable. The product is re-suspended to a given volume to have cells that are not too concentrated and to prevent de-hydration of cells.

The reagent addition step 20 involves adding a specific volume of magnetic beads and/or a cell staining agent or an activation reagent, In the incubation step 30, the cells are mixed with added reagent during a specific time inside or outside the centrifugal processing and separation chamber, for instance of a Sepax system. If this is done outside, place the cell bag on a device like the Smart-Max for mixing and temperature control.

The post-wash step 50 serves to remove reagent (e.g. beads), as applicable

Application 2: Virus Transduction with Lymphocytes T Cells

The second application relates to the transduction of lymphocytes T cells, or other human cells such as hematopoietic stem cells, by the addition of a virus.

This application illustrates the sequential carrying out of the following procedures: washing, dilution, transduction, dilution, volume adjustment.

The first stage is to precondition the cell-based product, usually coming from an apheresis procedure for collecting peripheral blood stem cells or from expanded cells after a cell culture process, by performing a washing procedure in order to remove unwanted elements such as platelets, aggregates, clots or cell debris. Once unwanted elements are removed, cells are also rehydrated by adding biological nutriments and could be suspended in a fixed desired volume. Medium culture should also be removed if cells were previously cultured and also Dimethyl sulfoxide if the product was previously cryopreserved.

Then, the second stage consists of diluting the pre-conditioned biological product in stage 1 with a solution containing the virus later used for transduction. In this context, usually the solution containing the virus is primed inside the centrifugation chamber containing the cells.

The third stage consists of spinning at a high speed, between 1200 to 1700 g, in order to separate cells from suspension media and putting them in close contact with the virus for initiating a transduction process. By spinning at high g-forces, T lymphocytes will separate from media and will stick to the external surface of the centrifugation chamber. At the same time, virus inserted in the chamber will be spread in the fluid in the separation chamber, and close contact will initiate the transduction process of T lymphocytes cells with the virus.

At the end of the high-spin process, the solution is then diluted with a culture medium solution, or saline solution, in order to reach the desired final volume.

Finally, the entire solutions can be split in one or several solution bags if the dose needs to be used several times for later use.

Figure 2A:
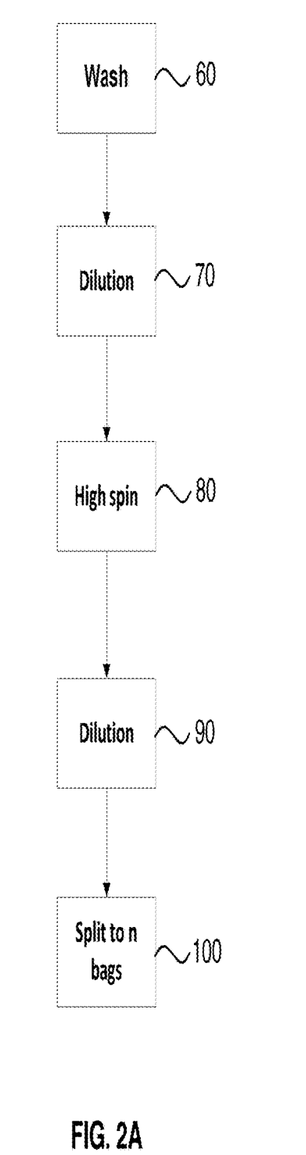
FIG. 2A is a flow diagram of a second application of the invention.
Figure 2B:
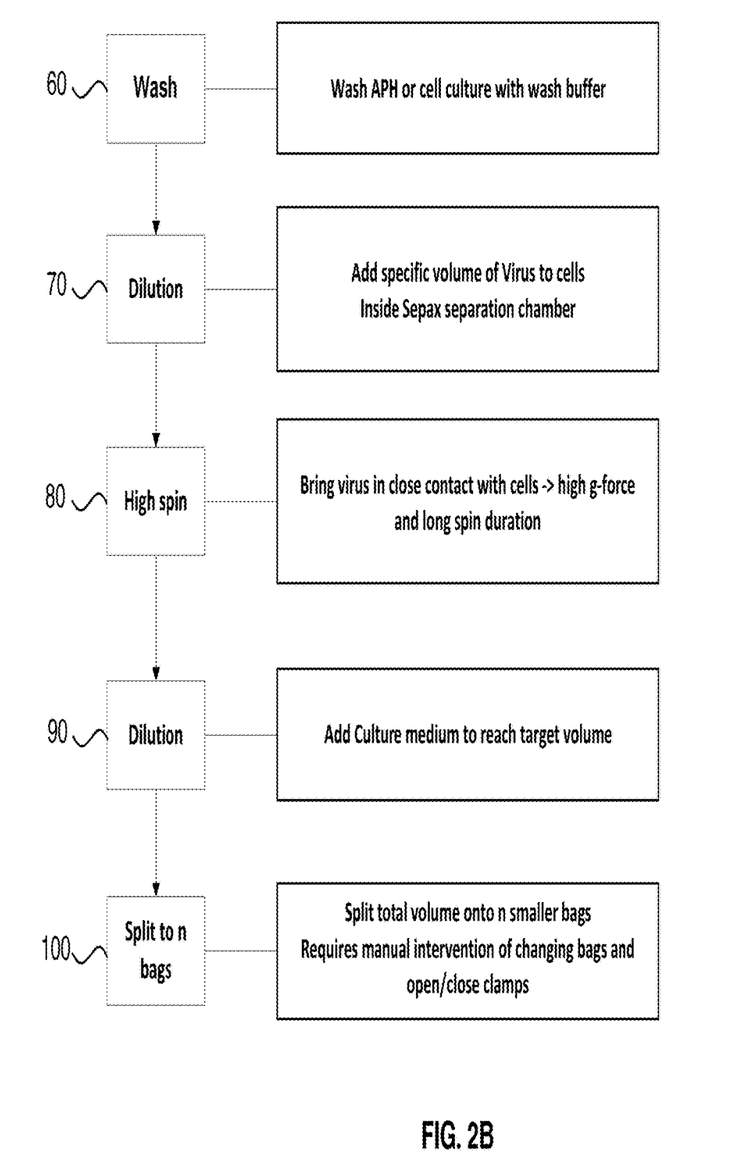
FIG. 2B is a completed diagram of the second application.

This second application is illustrated in FIG. 2A and FIG. 2B. As shown in FIG. 2A, this application of the process includes a wash step 60, followed by dilution 70 and a high-spin operation 80, then dilution 90 and an optional splitting step 100 for splitting the product into n bags.

As indicated in FIG. 2B:
The washing step 60 washes a cell-based product, usually coming from an apheresis procedure, or a cell culture, with a wash buffer.
In the dilution step 70, a specific volume of virus is added to the cells inside the separation chamber of a Sepax system.
This is then subjected to a high-spin step 80 in the Sepax centrifugal processing chamber to bring the virus into close contact with the cells, though a high g-force and a long spin duration.
In the dilution step 90 culture medium is added to reach a target volume.
In the splitting step 100, the total volume is split into n smaller bags. This requires manual intervention to change bags and open/close clamps.

Application 3: Recondition Dosing (after Cryo, Including Accurate Dosing for Patient Infusion)

This application illustrates the sequential carrying out of the following procedures: washing, separation, dilution, volume adjustment.

Usually, in a standard autologous transplantation set-up, aphaeresis procedures are performed in pre-conditioned patients. Peripheral blood, which is enriched of blood cells and hematopoietic stem cells due to the pre-conditioning of the patient, is cryopreserved during the time the patient is undergoing chemotherapies or radiotherapies. Once the patient has been treated, patient cells are thawed and reconditioned prior to being transplanted.

The third application is a repeatable automated method for obtaining multiple doses of cellular products having identical blood cells or stem cells concentration starting from a cryopreserved apheresis solution.

The first stage relates to thawing a cellular product under a controlled temperature and mixing environment for example using the device described in WO 2014/181158 A1, and commercialised by Biosafe SA under the Trademark Smart-Max. Such devices are for mixing biological specimens contained in flexible storage bags at controlled temperature, which flexible storage bags may serve, in addition to storage, for the collection, freezing storage or transfer of biological specimens, Then, the second stage consists of performing a washing procedure that will eliminate cryo-protectant solution, aggregates formed during the cryopreservation process or even clots.

Then, the third stage consists of taking a sample for measuring cell concentration. The sample is analysed via a tierce technology, such as cell counter or flow-cytometer, necessary for cell concentration calculation. Once the actual density of cells has been calculated, a dilution factor is adjustable on an automated Sepax platform in order to reach the desired cell concentration. Those two previous steps allow a reproducible and homogenized cell concentration to be obtained independently of the collection process or the patient.

Once a targeted cell concentration is obtained, the Sepax system allows the user to select the volume that should be divided on each bag, or the number of bags that should contain the total cell solution. By doing so, a fixed number of bags or volume dose per bag, all containing an identical cell concentration can be achieved.

Figure 3A:
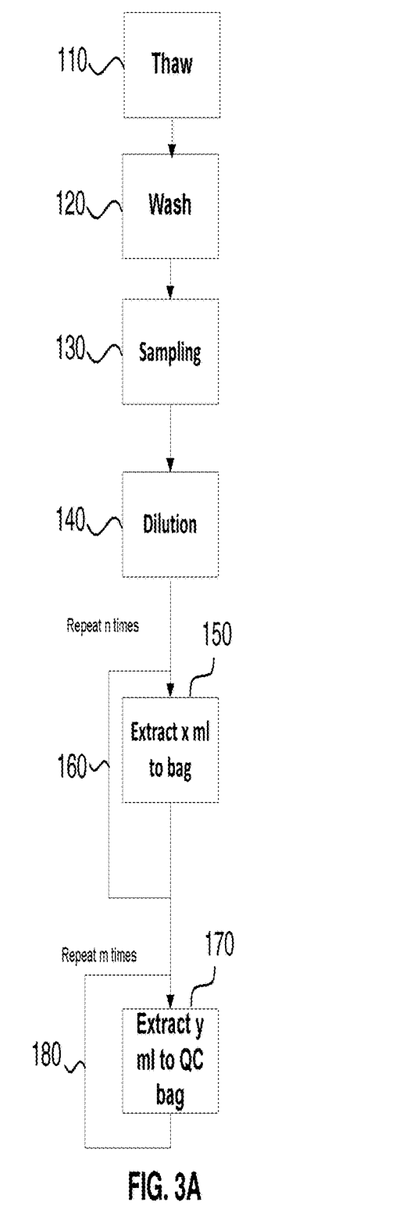
FIG. 3A is a flow diagram of a third application of the invention.
Figure 3B:
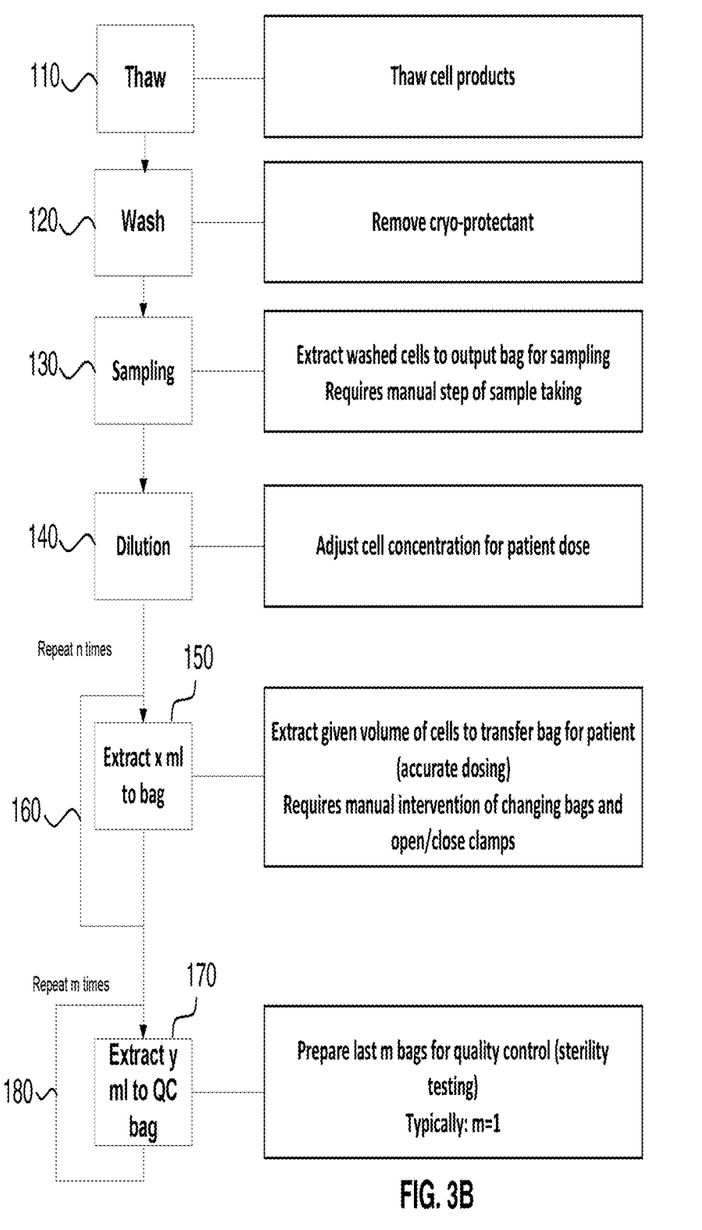
FIG. 3B is a completed diagram of the third application.

This third application is illustrated in FIG. 3A and FIG. 3B. As shown in FIG. 3A, this application of the process includes a thawing step 110, followed by washing 120, sampling 130 and dilution 140. A first extraction step 150 extracts x ml to a bag, repeated n times via loop 160, A second extraction step 170 extracts y ml to a Quality Control bag, this step being repeated m times via loop 180 typically only once.

As indicated in FIG. 3B:
Thawing operation 110 serves to thaw cell products.
In washing operation 120, cryo-protectant is removed.
In sampling operation 130, washed cells are extracted to an output bag for sampling. This operation requires the manual step of sample taking.
In dilution step 140, the cell concentration is adjusted for patient dosing.
The first extraction step 150 extracts a given volume of cells to a transfer bag for accurate patient dosing. This requires manual intervention to change bags and open/close clamps.
The second extraction step 170 prepares the last m bags for Quality Control (sterility testing). Typically, m=1.

Figure 4:
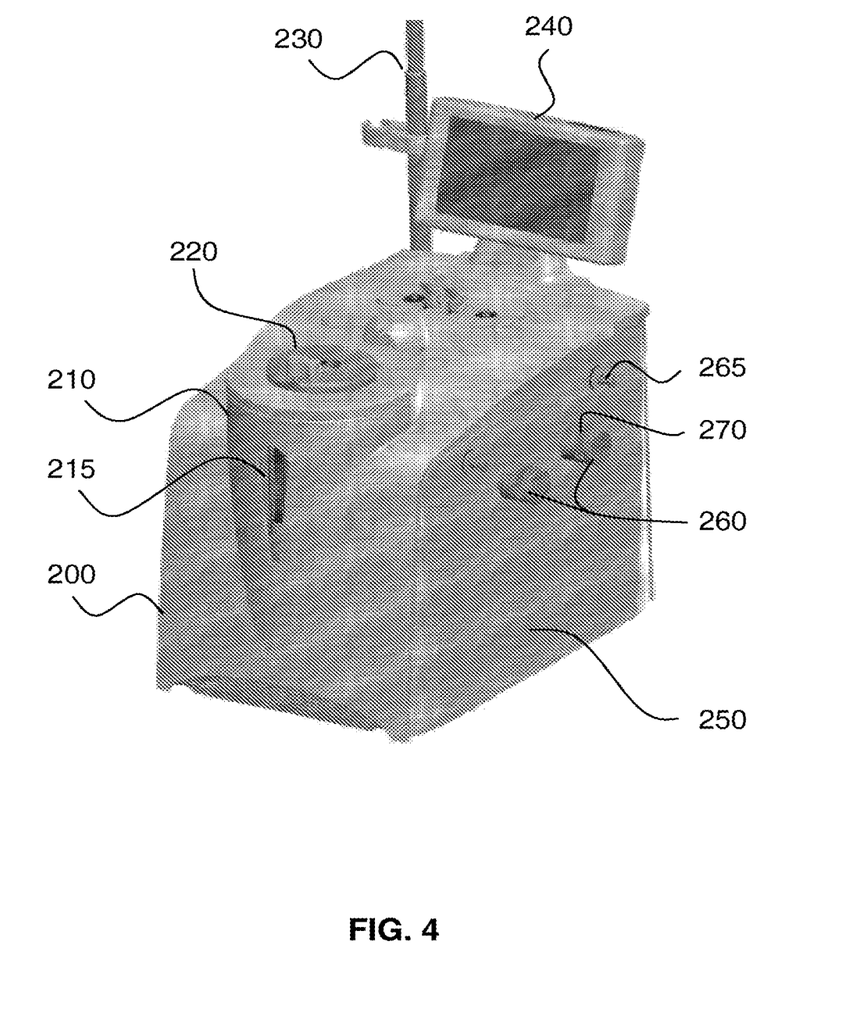
FIG. 4 is a perspective view of a cabinet for housing the processing chamber of an apparatus for carrying out the process according to the invention.

FIG. 4 is a perspective view of a cabinet 200 for housing the processing chamber of an apparatus for carrying out the invention, which apparatus is part of a system according to EP-B-0 912 250 and EP-B1 144 026, the contents whereof are herein incorporated by way of reference. As shown the cabinet 200 has a front with an upwardly-protruding part-cylindrical housing 210 having on top a swinging closure 220 for receiving inside the generally cylindrical centrifugal processing chamber (not shown) of the system. In its bulging front, the part-cylindrical housing 210 has a window 215 for viewing an inserted cylindrical processing chamber and its contents. At the rear of the cabinet 200 is an upwardly-extending post (shown partly cut-away) for suspending bags of a disposable set. Also at the rear of cabinet 200 is a display screen 240 for displaying parameters of the processing protocol according to integrated software. The sides 250 of cabinet 200 are flat and at least one of these flat sides 250 is provided with two pinch valves 260 having slots 270 for accomodating tubing of a disposable set associated with the cabinet 200, this tubing leading to two bags of the disposable set supported on the cabinet's sides 250. Above the pinch valves 260 are protrusions 265 for guiding the tubing. These two pinch valves 260 can be arranged for automatically selecting, by the software associated with the cabinet 200, two biological additives such as virus, for priming the processing chamber and later switching with the medium solution for resuspension, enabling switching bags without user intervention.

Figure 5:
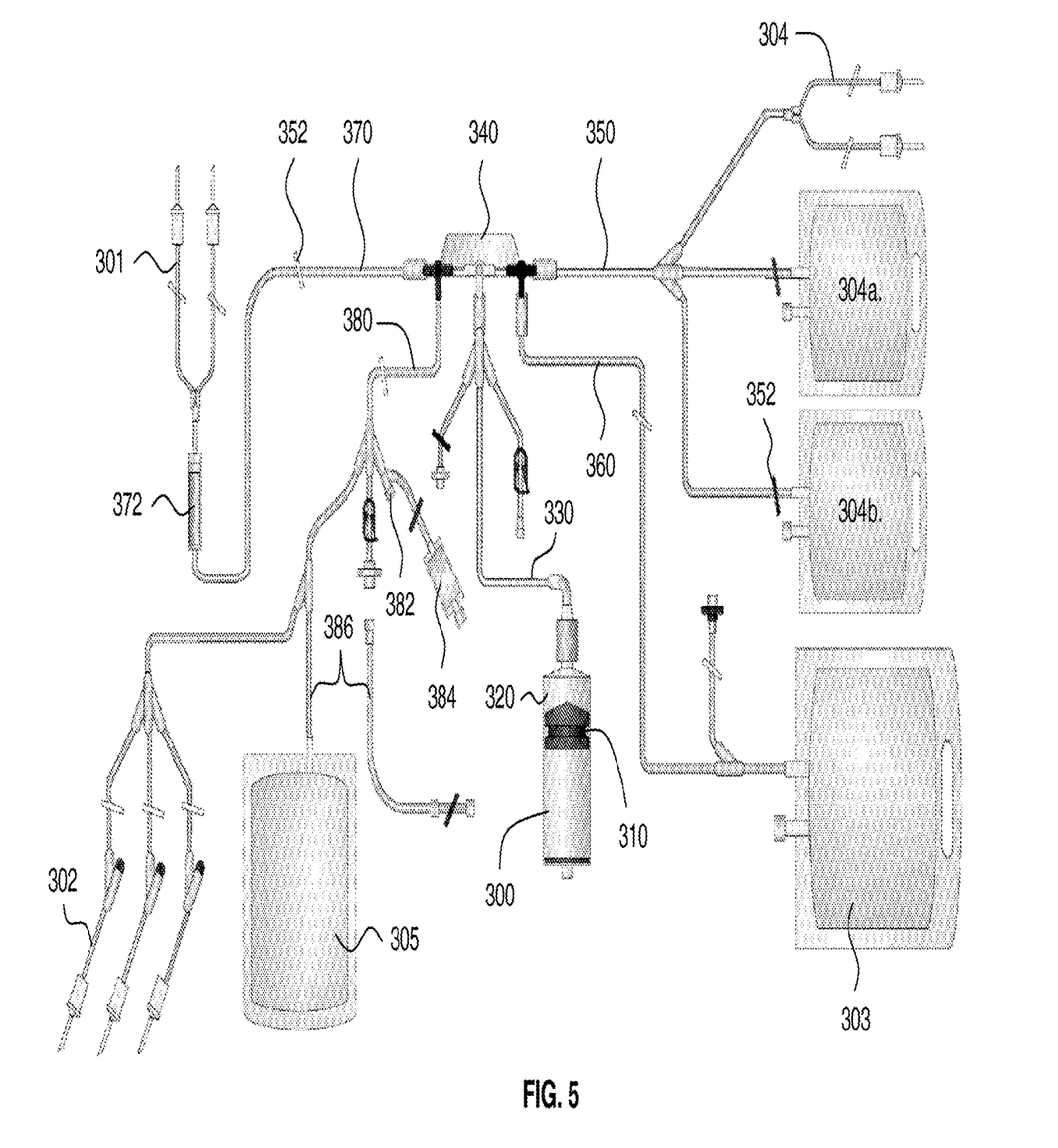
FIG. 5 is a diagram of a disposable kit or set usable in the process according to the invention for carrying out the given applications.

FIG. 5 schematically shows the layout of a disposable set or kit for use in the process according to the invention to carry out all of the three described applications. The disposable set comprises a centrifugal processing chamber 300 containing a movable member or piston 310 that defines a processing space 320 of variable volume in the chamber 300. The chamber 300 is connected via a tubing line 330 to a 5-way valve 340. One outlet of the valve 340 is connected by a tubing line 350 which branches out to connect to input spikes 304 for saline solutions or other solutions and to bags 394a and 304b for saline solutions or various other products. Another outlet of valve 340 is connected by a tubing line 360 to a waste bag 303. A third outlet of valve 340 is connected via a tubing line 370 and a filter 372 to input spikes 301 for the connection of blood bags or bags of other biological fluids. A fourth outlet of valve 340 is connected via a tubing line 380 to a set of output spikes 302, and branched off to a collection bag 305. The tubing line 380 also leads to a sampling port 382 and a sampling pillow 384.

The various tubing lines are fitted with pinch valves 352 that can be manually actuated when the disposable set is being set up, or some can be automatically operated during use, see for example the magnetically-operated pinch valves 260, FIG. 4.

The described kit or disposable set forms an enclosed sterile environment, even with bags connected to the spikes 301, 302 and 304.

BeadWash

For the beadwash application, one or two apheresis blood units can be connected to the kit via the input spikes 301. Then the blood apheresis units are filtered through the input filter 372 for removing any debris, clots and any unwanted residuals.

The pre-wash step consist of washing cells, and for this a washing solution, such as a saline solution NaCl is connected either using the spikes 304 or filled in one available bag 304a. Once the pre-washing step finished, waste solution is redirected in waste bag 303 and cells remain in the chamber 300.

Then the second step consists of adding reagent including magnetic beads in the processing chamber 300, that has been filled in the second available bag 304b. Then an incubation step is done inside chamber 300.

Finally, a post-wash step is done by pumping the same saline solution as in the pre-washing step, and finally incubated cells with magnetic beads are extracted in the collection bag 305, or in any custom bag connected by a spike 302.

Transduction

With the virus transduction application, the first step consists of connecting the apheresis unit(s) with the input spike(s) 301, connecting saline solution with spikes 304, adding a solution containing the virus in a bag 304a, adding a medium solution for cell nutriment in bag 304b, and finally connecting multiple output bags, up to three bags, via spikes 302.

The first step consists of pumping apheresis unit via input bag in 1, then washing via the saline solution connected by spikes 304, then cells remain in the chamber 300 and the virus solution (from bag 304a) is added to the chamber 300, the solution is centrifuged with a high spin force, then the solution is suspended in a culture medium from bag 304b, and finally the solution is split into equivalent or different volumes in up to three bags connected to spikes 302.

Reconditioning and Dose

With this application, first a cryopreserved blood unit is thawed. Then the bag of thawed blood solution is connected to input spike 301 and the solution pumped into chamber 300. Then, the previously-connected saline solution is connected via spikes 304 or an available bag 403a is used to wash the apheresis unit in the chamber 300. Once the cells are washed, a partial or total cell solution in the chamber 300 is extracted in the collection bag 305, followed by a sample taken for measuring cell concentration via the sampling port 382. Then, the volume can be pumped inside the chamber 300 again, diluted with saline solution from a bag connected to spike 304 or an available bag 304a, and then split in several bags connected on the output spikes 302.

The kit optionally includes a cryopreparation line with a sampling pillow 384 in case a sample needs to be taken outside the laminar flow, and a DMSO resistant in the tubing path 386 in case the final solution needs to be added with cryoprotectant solution for further freezing.

What is claimed is:

1. A system for sequentially processing biological fluids comprising:
   (a) a cabinet defining at least one flat side provided with two external pinch valves having slots for accommodating tubing and controlling passage of fluid through tubing in the slots; and
   (b) a disposable set disposed within the cabinet comprising,
      (i) a cylindrical centrifugal processing chamber having a movable member being disposed within the centrifugal processing chamber and defining a separation space in an upper portion of the processing chamber;
      wherein, the movable member is axially movable to vary the volume of the separation space within the processing chamber to intake or to output fluid into or from the separation space;
      (ii) a set of inputs connected to the processing chamber via tubing at one end, and connected to a plurality of solution bags containing biological fluids or additives to be transferred into the processing chamber at an opposite end wherein respective tubing from two solution bags of the plurality of solution bags passes through the respective slots of the two external pinch valves; and
      (iii) a central valve connected to the processing chamber and the inputs via tubing, the tubing having a plurality of pinch valves, wherein the central valve is a five-way valve;
      wherein the central valve is connected to (a) a waste bag of the disposable set via tubing, (b) a collection bag of the disposable set via tubing, (c) to the two solution bags of the plurality of solution bags; and (d) to a set of outputs via tubing branched off from the collection bag, wherein, the arrangement of pinch valves and the central valve facilitates an automated and sequential transfer of each of the biological fluids and the additives to the processing chamber and is configured to perform in the processing chamber a chained sequence comprising at least three different sequentially chained procedures by operating the pinch valves and the central valve to direct flow through the tubing between the inputs, the waste bag, the collection bag, and the outputs, wherein the chained sequence constituting an overall sequential operation in the processing chamber comprises one of the following sequences of procedures (i), (ii) and (iii):

(i) pre-washing; addition of reagents and incubation; post-washing, (ii) washing; dilution; centrifugal separation; dilution; volume adjustment of the product, and (iii) preliminary thawing; washing; sampling and dilution; volume adjustment/extraction.

2. The system of claim 1, wherein procedures selected from washing, incubation, transduction, separation, density gradient separation, dilution and volume adjustment, are carried out by the system.

3. The system of claim 2, wherein each of the procedures is carried out once or repeated a number of times according to a given processing profile in the processing chamber of the disposable set.

4. The system of claim 1, wherein the biological fluids include whole blood, apheresis blood, bone marrow blood, umbilical cord blood, buffy coat and cultured cells.

5. The system of claim 1, wherein the movable member is a piston.

6. The system of claim 1, wherein the following procedures are carried out sequentially: pre-washing; addition of reagents and incubation; post-washing.

7. The system of claim 6, wherein the application of the procedures is for binding magnetic beads with human blood cells or stem cells.

8. The system of claim 1, wherein the following procedures are carried out sequentially: washing; dilution; centrifugal separation; dilution; volume adjustment of the product.

9. The system of claim 8, wherein the application of the procedures is for virus transduction with lymphocytes T-cells or other human cells.

10. The system of claim 1, wherein the following procedures are carried out sequentially: preliminary thawing; washing; sampling and dilution; volume adjustment/extraction.

11. The system of claim 10, wherein the application of the procedures for recondition dosing of multiple doses of cellular products.

12. The system of claim 1, wherein the position of the movable member is monitored by an infrared sensor.

13. The system of claim 1, wherein the volume of liquids treated in the processing chamber of the disposable set for one overall sequential operation is from four to sixteen times the maximum treatment volume of the processing chamber.

14. The system of claim 1, wherein the two solution bags respectively comprise two biological additives.

* * * * *